United States Patent [19]
König et al.

[11] Patent Number: 5,827,901
[45] Date of Patent: Oct. 27, 1998

[54] PROCESS OF PRODUCING METHANOL

[75] Inventors: Peter König, Frankfurt am Main; Hermann Göhna, Bad Soden, both of Germany

[73] Assignee: Metallgesellschaft Aktiengesellschaft, Frankfurt am Main, Germany

[21] Appl. No.: 792,325

[22] Filed: Jan. 31, 1997

[30] Foreign Application Priority Data

Feb. 15, 1996 [DE] Germany .................. 196 05 572.5

[51] Int. Cl.⁶ ................................. C07C 27/00
[52] U.S. Cl. .................... 518/706; 518/703; 518/707; 518/705
[58] Field of Search .................... 518/706, 703, 518/707, 705

[56] References Cited

U.S. PATENT DOCUMENTS

| | | | |
|---|---|---|---|
| 4,559,207 | 12/1985 | Hiller et al. | 518/703 |
| 5,216,034 | 6/1993 | Sie | 518/706 |
| 5,631,302 | 5/1997 | Konig et al. | 518/706 |

FOREIGN PATENT DOCUMENTS

| | | |
|---|---|---|
| 0047345 | 3/1982 | European Pat. Off. . |
| 2203427 | 10/1988 | United Kingdom . |

OTHER PUBLICATIONS

Industrial Engineering Chemical Research v 28 n 6 pp. 763–771, Jun. 1989.

Primary Examiner—Paul J. Killos
Assistant Examiner—Jafar Parsa
Attorney, Agent, or Firm—Sprung Kramer Schaefer & Briscoe

[57] ABSTRACT

Methanol is catalytically produced from a synthesis gas containing hydrogen and carbon oxides on copper-containing catalysts at pressures in the range from 20 to 120 bar and temperatures in the range from 130° to 350° C. The synthesis gas is first of all passed through a first synthesis reactor, in which the catalyst is provided in tubes surrounded by water as a coolant which is boiling at an elevated pressure. From the first reactor a first mixture containing gases and methanol vapor is withdrawn and passed through a second synthesis reactor. In the second reactor the catalyst is cooled with synthesis gas.

7 Claims, 1 Drawing Sheet

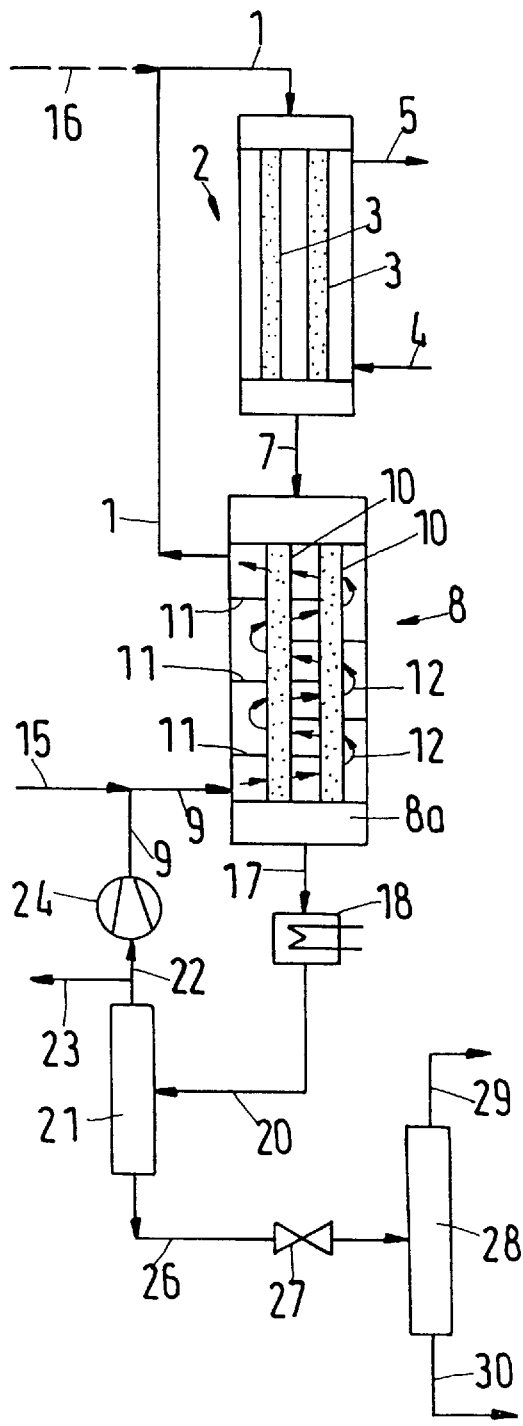
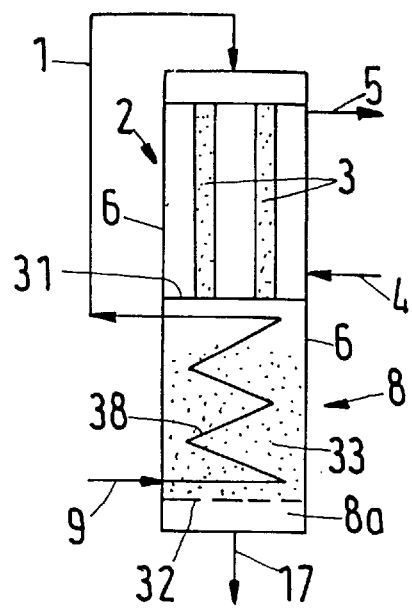
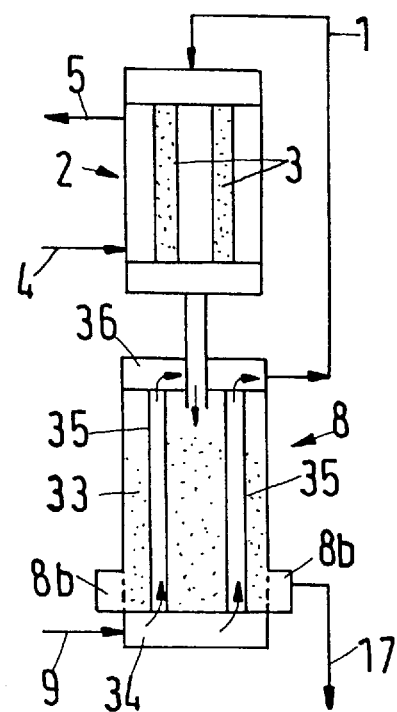
Fig.1
Fig.2
Fig.3

PROCESS OF PRODUCING METHANOL

This invention relates to a process of producing methanol from a synthesis gas containing hydrogen and carbon oxides through conversion on granular, copper-containing catalysts at pressures in the range from 20 to 120 bar and temperatures in the range from 130° to 350° C., where the synthesis gas is passed through at least two synthesis reactors connected in series.

Such process is described in DE-A-4416425. The synthesis gas is first of all passed through an adiabatically operated shaft reactor and then through a water-cooled tubular reactor. Both types of reactor, the shaft reactor and the tubular reactor, belong to the known technology of the catalytic production of methanol.

The object underlying the invention is to provide an inexpensive process on the basis of the tubular reactor. With this process it is possible to design the water-cooled tubular reactor as small as possible. In the above-stated process, this object is solved in accordance with the invention in that a) fresh and recycled synthesis gas, which has been preheated to a temperature in the range from 220° to 280° C., is introduced into the first synthesis reactor, in which the catalyst is provided in tubes surrounded by water as a coolant, which is boiling at an elevated pressure, b) in the first synthesis reactor 40 to 80% of the introduced carbon oxides are converted, and a first mixture containing gases and methanol vapor is withdrawn, c) the first mixture is passed through at least a second synthesis reactor, in which the catalyst is cooled with synthesis gas, that a second mixture containing gases and methanol vapor is withdrawn from the second synthesis reactor, the second mixture is cooled, and methanol vapor is condensed, and d) synthesis gas to be recycled is separated from the methanol-containing condensate, at least part of the separated synthesis gas is passed through the second synthesis reactor as a coolant, and the preheated synthesis gas is returned to the first reactor, where fresh synthesis gas coming from an external source is admixed to the synthesis gas to be recycled.

In the second synthesis reactor, the catalyst is generally cooled indirectly by the synthesis gas serving as coolant. However, a direct cooling is also possible, where a partial stream of the synthesis gas to be recycled is branched off and added to the first mixture coming from the first reactor, with the mixture being cooled in this manner.

In the process in accordance with the invention, the first synthesis reactor can be designed much smaller than in known processes comprising only one single reactor. In the water-cooled first reactor the conversion can be effected at relatively high temperatures in the process in accordance with the invention, so that advantageously a higher-pressure steam is produced. At the same time, the first mixture is discharged from the first reactor at a relatively high temperature and is directly introduced into the second synthesis reactor without an intermediate cooling. In the second synthesis reactor counter-currently cooled with synthesis gas, the temperatures in the vicinity of the outlet are rather low, which is advantageous for the synthesis of methanol. In the second reactor, the catalyst can be provided in tubes or chambers, around which flows the gaseous coolant. In the second reactor there can also be provided a catalyst bed, through which extend cooling tubes through which flows the synthesis gas. The second reactor can also comprise a plurality of series-connected partial reactors.

Advantageously, the synthesis gas introduced into the first synthesis reactor consists of 15 to 40 vol.-% fresh synthesis gas. Due to this relatively high content of fresh synthesis gas only a relatively small amount of synthesis gas is recycled, so that the required compression is less expensive.

The catalysts to be used are known and commercially available. In addition to CuO they also contain for instance ZnO and $Al_2O_3$.

The amounts of catalyst contained in the first and the second reactor will usually have a weight ratio in the range from 3:2 to 1:4. Preferably, this weight ratio lies in the range from 1:1 to 1:3. Thus, it is very well possible that the second reactor contains a larger amount of catalyst than the first reactor. It has turned out that the entire amount of catalyst is about the same or only slightly larger than in known processes of methanol synthesis, which only operate with the water-cooled tubular reactor.

Since the first synthesis reactor need not ensure a fairly high conversion of carbon oxides, this first reactor can be charged with a large amount of synthesis gas. Usually, the gas load for this first reactor lies in the range from 14,000 to 24,000 $Nm^3$ per hour and per $m^3$ catalyst. The first mixture withdrawn from the first synthesis reactor usually contains 4 to 10 vol.-% methanol vapor. The second mixture withdrawn from the second reactor mostly has temperatures in the range from 130° to 240° C.

Embodiments of the process will now be explained with reference to the drawing, wherein:

FIG. 1 shows a flow diagram of the process,

FIG. 2 shows a compact design of the two synthesis reactors, and

FIG. 3 shows a further variant of the two reactors.

With reference to FIG. 1, a mixture of fresh and recycled synthesis gas is introduced through line (1) into the first synthesis reactor (2). This first reactor is a tubular reactor known per se, in which the copper catalyst is provided in tubes (3). Water boiling at an elevated pressure is used as coolant, which is supplied via line (4). A mixture of boiling water and steam is withdrawn via line (5) and supplied to a not represented steam drum known per se. The synthesis gas entering the reactor (2) has been preheated to a temperature in the range from 220° to 280° C., the pressure lies in the range from 20 to 120 bar, and mostly in the range from 40 to 100 bar. The coolant withdrawn via line (5) usually has a temperature in the range from 240° to 280° C.

In the first reactor (2) 40 to 80% of the carbon oxides introduced into the reactor through line (1) are converted.

From the reactor (2) a first mixture consisting of gases and vapours is withdrawn via line (7), where the methanol content is 4 to 10 vol.-% and mostly 5 to 8 vol.-%. Without cooling the first mixture, the same is directly introduced into the second synthesis reactor (8), which is likewise designed as a tubular reactor. In the reactor (8) synthesis gas is used as cooling medium, which is supplied via line (9). To intensify the cooling of the tubes (10) containing the copper catalyst, the space in the reactor (8) through which flows the cooling gas is provided with baffles (11). Said baffles (11) provide a tortuous flow path for the cooling gas, which is indicated by the arrows (12). The synthesis gas serving as coolant is preheated in the reactor (8) and then flows through line (1) to the first synthesis reactor (2). Fresh synthesis gas, which is produced in a not represented plant known per se, is supplied via line (15) and admixed to the synthesis gas to be recycled. It is also possible to supply fresh synthesis gas through line (16) and add it to line (1). It is ensured that the synthesis gas, which enters the first reactor (2), contains hydrogen and carbon oxides in about the following proportions:

$H_2$ =40 to 80 vol.-%,

CO=3 to 15 vol.-%, and $CO_2$ =1 to 10 vol.-%.

In the gas-cooled reactor (8) the temperatures in the catalyst in the vicinity of the outlet chamber (8a) lie in the range from 130° to 240° C., and usually in the range from 160° to 220° C. Due to these relatively low temperatures, the formation of methanol in the gas mixture flowing through the catalyst is promoted.

A product mixture containing gases and methanol vapor, which is also referred to as second mixture, leaves the reactor (8) through line (17) and flows through the indirect cooler (18), where methanol is condensed. Subsequently, the mixture is supplied through line (20) to a first separating vessel (21), in which gases and liquid are separated. The gases are withdrawn through line (22), where part of the gases are removed from the process through line (23). As has already been described, the gases are first of all supplied as synthesis gas to be recycled through line (9) to the reactor (8) by means of the compress or (24).

Methanol-containing liquid is withdrawn from the first separating vessel (21) through line (26), and through a pressure reducing valve (27) the liquid is supplied to a second separating vessel (28), from which a residual gas is withdrawn through line (29), and in line (30) raw methanol is obtained, which is cleaned by distillation in a manner known per se, which is not represented here.

FIG. 2 shows a compact design for the two reactors (2) and (8), which are accommodated in a common housing (6). Between them, the liquid-tight partition (31) is provided. On a grid (32), the second reactor (8) comprises a catalyst bed (33), through which extends a coolant line (38). The first mixture coming from the tubes (3) flows downwards through said bed to the chamber (8a). The remaining reference numerals have the meaning described already, which is also true for FIG. 3. The second reactor (8) contains the catalyst bed (33), through which flows the first mixture containing gases and methanol vapor, which comes from the first reactor (2). The second mixture first of all reaches the outer collecting chamber (8b) and is withdrawn via line (17). The synthesis gas supplied via line (9) first of all enters a distribution chamber (34) and then flows upwards through the tubes (35) as cooling gas. Having been collected in the chamber (36), the synthesis gas is supplied to the first reactor (2) via line (1).

EXAMPLES

The inventive mode of operation of Examples 2 and 4 is based on the arrangement shown in FIG. 1, but without line (16). In Comparative Examples 1 and 3 only the boiling-water-cooled reactor (2) is used, but not the reactor (8) cooled with synthesis gas. The data of the Examples have been calculated in part. The catalyst used in all cases is a commercially available catalyst and consists of 60 wt-% CuO, 30 wt-% ZnO and 10 wt-% $Al_2O_3$. In the following Table I "line (15)" stands for the composition of the fresh synthesis gas supplied via line (15), and "line (1)" stands for the composition of the synthesis gas entering the reactor (2) via line (1). The amount of fresh synthesis gas is the same in all Examples, and the data are based on 1 Kmol/h.

TABLE I

|  | Example 1 | Example 2 | Example 3 | Example 4 |
|---|---|---|---|---|
| Line (15): |  |  |  |  |
| $H_2$ (mole-%) | 70.7 | 70.7 | 68.1 | 68.1 |
| CO (mole-%) | 17.2 | 17.2 | 21.0 | 21.0 |
| $CO_2$ (mole-%) | 7.9 | 7.9 | 7.7 | 7.7 |
| Inert gases (mole-%) | 4.2 | 4.2 | 3.2 | 3.2 |
| Line (1): |  |  |  |  |
| $H_2$ (mole-%) | 74.6 | 74.5 | 61.3 | 61.7 |
| CO (mole-%) | 5.3 | 5.7 | 5.9 | 6.5 |
| $CO_2$ (mole-%) | 4.3 | 4.5 | 4.8 | 5.1 |
| $CH_3OH$ (mole-%) | 0.3 | 0.3 | 0.5 | 0.5 |
| Others (mole-%) | 15.5 | 15.0 | 27.5 | 26.2 |
| Temperature | 220° C. | 225° C. | 230° C. | 235° C. |
| Pressure | 70 bar | 70 bar | 81 bar | 81 bar |

In Example 2, which is operated with two synthesis reactors (2) and (8), the entire amount of catalyst is only 1.06 times higher than in Comparative Example 1 with its single reactor (2). In Example 2, the entire amount of catalyst is distributed over the reactors (2) and (8) with a ratio of 40:60. In Example 1, the mass ratio ("circuit ratio") of fresh synthesis gas in line (15) to the synthesis gas to be recycled, which comes from the compressor (24), is 1:3.3, and in Example 2 the circuit ratio is about 1:2.5, so that a minor amount of gas flows through line (1).

In Example 1 saturated steam of 40 bar is produced when cooling the tubular reactor, whereas in accordance with Example 2 saturated steam of 50 bar can be discharged through line (5).

In Example 1, the catalyst is loaded with 11,000 $Nm^3$ synthesis gas per $m^3$ and per hour, whereas in the tubular reactor (2) of Example 2 a loading of 20,000 $Nm^3/m^3/h$ is achieved. In Example 3 (Comparative Example), the loading is 12,000 $Nm^3/m^3/h$, and in Example 4 in accordance with the invention the tubular reactor (2) is operated with a loading of 18,000 $Nm^3/m^3/h$. In Example 3, the circuit ratio is 1:4, and in Example 4 it is 1:2.7.

Table II shows the concentration of a few important components of the gas and vapor mixture at the outlet of the reactor (2) and at the outlet of the reactor (8):

TABLE II

|  | Example 1 | Example 2 | Example 3 | Example 4 |
|---|---|---|---|---|
| Outlet reactor (2): |  |  |  |  |
| $CH_3OH$ (mole-%) | 6.6 | 5.0 | 6.8 | 5.7 |
| $CO_2$ (mole-%) | 3.0 | 3.5 | 3.8 | 4.4 |
| CO (mole-%) | 1.6 | 3.0 | 2.0 | 3.3 |
| $H_2$ (mole-%) | 69.6 | 70.7 | 54.9 | 56.4 |
| Others (mole-%) | 19.2 | 17.8 | 32.5 | 30.2 |
| Temperature | 253° C. | 268° C. | 255° C. | 264° C. |
| Outlet reactor (8): |  |  |  |  |
| $CH_3OH$ (mole-%) | — | 8.3 | — | 9.4 |
| $CO_2$ (mole-%) | — | 2.9 | — | 3.8 |
| CO (mole-%) | — | 1.0 | — | 1.0 |
| $H_2$ (mole-%) | — | 68.0 | — | 52.7 |
| Others (mole-%) | — | 19.8 | — | 33.1 |
| Temperature | — | 180° C. | — | 186° C. |

In Example 4 the entire amount of catalyst, which is distributed over the reactors (2) and (8) in a ratio of 42:58, is 15% higher than in Example 3. In reactor (2) of Example 3, which is cooled with boiling water, the temperature of the discharged coolant is 250° C., and in Example 4 this temperature is 260° C.

We claim:

1. A process of producing methanol from a synthesis gas containing hydrogen and carbon oxides through conversion of said synthesis gas on a granular, copper-containing catalyst at pressures in the range from 20 to 120 bar and temperatures in the range from 130° to 350° C., where the synthesis gas is passed through a first and a second synthesis reactor connected in series, said two reactors containing fixed beds of said catalyst, comprising the steps of:

a) producing a feed mixture of fresh and recycled synthesis gas preheated to a temperature in the range from 220° to 280° C., introducing said feed mixture into the first synthesis reactor, in which the catalyst is provided in tubes surrounded by water as a coolant which is boiling at an elevated pressure, b) in the first synthesis reactor 40 to 80% of the introduced carbon oxides are converted, and a first mixture containing gases and methanol vapor is withdrawn, said first mixture is directly fed into the second synthesis reactor without an intermediate cooling, c) passing the first mixture through said second synthesis reactor, in which the catalyst is indirectly cooled with said feed mixture, withdrawing preheated feed mixture from said second reactor and feeding it into said first reactor, withdrawing a second mixture containing gases and methanol vapor from the second synthesis reactor, said second mixture is cooled and methanol vapor is condensed, a methanol containing condensate is withdrawn and a synthesis gas stream is separately withdrawn and is mixed with fresh synthesis gas to produce said feed mixture.

2. The process as claimed in claim 1, characterized in that the first mixture withdrawn from the first synthesis reactor contains 4 to 10 vol.-% methanol vapor.

3. The process as claimed in claim 1, characterized in that the second mixture is withdrawn from the second synthesis reactor at a temperature of 130° to 240° C.

4. The process as claimed in claim 1, wherein the synthesis gas introduced into the first synthesis reactor consists of 15 to 40 vol.-% fresh feed mixture.

5. The process as claimed in claim 1, wherein the amounts of catalyst contained in the first and second reactor have a weight ratio of 3:2 to 1:4.

6. The process as claimed in one of claim 1, characterized in that in the second synthesis reactor 40 to 80% of the carbon oxides introduced into the second reactor are converted.

7. The process as claimed in claim 1, wherein 14,000 to 24,000 $Nm^3$ synthesis gas per hour and per $m^3$ catalyst are introduced into the first synthesis reactor.

* * * * *